United States Patent

De Faveri et al.

(10) Patent No.: US 8,022,232 B2
(45) Date of Patent: Sep. 20, 2011

(54) METHOD FOR MANUFACTURE OF ESCITALOPRAM

(75) Inventors: Carla De Faveri, Farra di Soligo (IT); Florian Anton Martin Huber, Bolzano Vicentino (IT); Robert Dancer, Hvidovre (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 249 days.

(21) Appl. No.: 12/202,522

(22) Filed: Sep. 2, 2008

(65) Prior Publication Data

US 2009/0069582 A1  Mar. 12, 2009

Related U.S. Application Data

(60) Provisional application No. 60/971,443, filed on Sep. 11, 2007.

(51) Int. Cl.
*A61K 31/34* (2006.01)
*C07D 307/00* (2006.01)

(52) U.S. Cl. .................. 549/467; 514/469; 558/422

(58) Field of Classification Search .............. 514/467, 514/469; 558/422; 549/467
See application file for complete search history.

(56) References Cited

U.S. PATENT DOCUMENTS

| | | | |
|---|---|---|---|
| 3,446,620 | A | 5/1969 | Parker |
| 3,467,675 | A | 9/1969 | Peterson et al. |
| 3,578,452 | A | 5/1971 | Parker et al. |
| 4,136,193 | A | 1/1979 | Bogeso et al. |
| 4,943,590 | A | 7/1990 | Boegesoe et al. |
| 7,112,686 | B2 | 9/2006 | Humble et al. |
| 7,390,913 | B2 | 6/2008 | Petersen et al. |
| 2005/0065207 | A1 | 3/2005 | Sommer et al. |

FOREIGN PATENT DOCUMENTS

| | | |
|---|---|---|
| DE | 1543714 | 1/1970 |
| EP | 0171943 | 2/1986 |
| EP | 0347066 | 12/1989 |
| EP | 1 700 851 A1 | 9/2006 |
| WO | WO-03/000672 | 1/2003 |
| WO | WO-03006449 | 1/2003 |
| WO | WO-03/051861 A1 | 6/2003 |
| WO | WO-2004056754 | 7/2004 |
| WO | WO-2006106531 | 10/2006 |
| WO | WO-2007012954 | 2/2007 |
| WO | WO 2008/059514 A2 | 5/2008 |

*Primary Examiner* — Taylor Victor Oh

(74) *Attorney, Agent, or Firm* — Stephen G. Kalinchak; Mary Catherine Di Nunzio

(57) ABSTRACT

This patent discloses a method for resolution of 4-[4-(dimethylamino)-1-(4'-fluorophenyl)-1-hydroxybutyl]-3-(hydroxymethyl)-benzonitrile as a racemic or non-racemic enantiomer mixture into its isolated enantiomers, said method comprising the step of fractionally crystallizing 4-[4-(dimethylamino)-1-(4'-fluorophenyl)-1-hydroxybutyl]-3-(hydroxymethyl)-benzonitrile as a salt with the (+)-(S,S)- or (−)-(R,R)-enantiomer of O,O'-di-p-toluoyl-tartaric acid in a solvent system comprising 1-propanol, ethanol or acetonitrile.

22 Claims, No Drawings

METHOD FOR MANUFACTURE OF ESCITALOPRAM

TECHNICAL FIELD OF THE INVENTION

The present invention relates to a method for manufacture of the well-known anti-depressant escitalopram.

BACKGROUND OF THE INVENTION

Escitalopram is a well-known antidepressant drug that has the following structure:

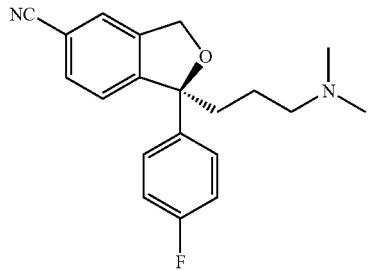

It is a selective, centrally active serotonin (5-hydroxytryptamine; 5-HT) reuptake inhibitor, accordingly having antidepressant activities.

Escitalopram and the pharmaceutical activity thereof are disclosed in U.S. Pat. No. 4,943,590. Two methods for preparation of escitalopram are disclosed. In one of them 4-[4-(dimethylamino)-1-(4'-fluorophenyl)-1-hydroxybutyl]-3-(hydroxymethyl)-benzonitrile is fractionally crystallized as a salt with (+)-O,O'-di-p-toluoyl-(S,S)-tartaric acid in 2-propanol. The crystalline product produced in this way consists of small crystals that drain very slowly and tend to retain the mother liquors. Insufficient removal of the mother liquors gives a product with a low enantiomeric purity and therefore additional purifications are required. Purifications are time and solvent consuming. These problems are more evident on an industrial scale.

SUMMARY OF THE INVENTION

It has now been found that resolution of 4-[4-(dimethylamino)-1-(4'-fluorophenyl)-1-hydroxybutyl]-3-(hydroxymethyl)-benzonitrile by fractional crystallization of 4-[4-(dimethylamino)-1-(4'-fluorophenyl)-1-hydroxybutyl]-3-(hydroxymethyl)-benzonitrile as a salt with (+)-(S,S)— or (−)-(R,R)—O,O'-di-p-toluoyl-tartaric acid in a solvent system comprising 1-propanol wherein not more than 0.5 mol (+)-(S,S)— or (−)-(R,R)—O,O'-di-p-toluoyl-tartaric acid is used per mol 4-[4-(dimethylamino)-1-(4'-fluorophenyl)-1-hydroxybutyl]-3-(hydroxymethyl)-benzonitrile results in a crystalline product wherein the crystals are larger and of a different shape than those from 2-propanol. This process has proven to be a robust and stable method for producing crystals with good filtering properties. This results in much better draining properties and reduced filtration times which have an important impact on large scale production. Typical filtration times for an industrial scale batch is a few hours or less.

This resolution method is useful in the manufacture of escitalopram.

DETAILED DESCRIPTION OF THE INVENTION

One aspect of the present invention is to provide a method for resolution of 4-[4-(dimethylamino)-1-(4'-fluorophenyl)-1-hydroxybutyl]-3-(hydroxymethyl)-benzonitrile as a racemic or non-racemic enantiomer mixture into its isolated enantiomers, said method comprising the step of fractionally crystallizing 4-[4-(dimethylamino)-1-(4'-fluorophenyl)-1-hydroxybutyl]-3-(hydroxymethyl)-benzonitrile as a salt with the (+)-(S,S)- or (−)-(R,R)-enantiomer of O,O'-di-p-toluoyl-tartaric acid in a solvent system comprising 1-propanol, ethanol or acetonitrile.

In a particular embodiment not more than 1 mol, more particularly not more than 0.5 mol, of the (+)-(S,S)- or (−)-(R,R)-enantiomer of O,O'-di-p-toluoyl-tartaric acid is used per mol of 4-[4-(dimethylamino)-1-(4'-fluorophenyl)-1-hydroxybutyl]-3-(hydroxymethyl)-benzonitrile.

In one embodiment (+)-O,O'-di-p-toluoyl-(S,S)-tartaric acid is used. In another embodiment (−)-O,O'-di-p-toluoyl-(R,R)-tartaric acid is used.

In a particular embodiment 1-propanol is the major constituent of the solvent system. In a more particular embodiment 1-propanol constitutes at least 50% of the solvent system, such as at least 75%, at least 90% or at least 95% and in a most particular embodiment 1-propanol is the only solvent.

In an equally particular embodiment ethanol is the major constituent of the solvent system. In a more particular embodiment ethanol constitutes at least 50% (v/v) of the solvent system, such as at least 75%, at least 90% or at least 95% and in a most particular embodiment ethanol is the only solvent.

In an equally particular embodiment acetonitrile is the major constituent of the solvent system. In a more particular embodiment acetonitrile constitutes at least 50% (v/v) of the solvent system, such as at least 75%, at least 90% or at least 95% and in a most particular embodiment acetonitrile is the only solvent.

In another embodiment the solvent system comprises one or more organic co-solvents, particularly selected from the group consisting of toluene, diethylether, ethyl acetate, dichloromethane and acetonitrile, more particularly toluene. In a more particular embodiment the amount of co-solvent is in the range of 0-20% (v/v) of the solvent system, such as 0-15%, 0-10%, 0.5-8%, 1-5% or 1.5-3%.

In yet another embodiment the solvent system comprises water. In a more particular embodiment the amount of water is in the range of 0-8% (v/v) of the solvent system, such as 0.05-5%, 0.1-3% or 0.15-2%.

In yet another embodiment the solvent system comprises an achiral acid, which is capable of protonating 4-[4-(dimethylamino)-1-(4'-fluorophenyl)-1-hydroxybutyl]-3-(hydroxymethyl)-benzonitrile but does not precipitate the 4-[4-(dimethylamino)-1-(4'-fluorophenyl)-1-hydroxybutyl]-3-(hydroxymethyl)-benzonitrile as a salt in the present conditions. In a particular embodiment the achiral acid is selected from the group consisting of organic acids such as formic acid, acetic acid, trifluoroacetic acid and methanesulfonic acid, more particularly acetic acid. In a more particular embodiment the amount of achiral acid is in the range of 0-0.5 equivalents relative to the amount of 4-[4-(dimethylamino)-1-(4'-fluorophenyl)-1-hydroxybutyl]-3-(hydroxymethyl)-benzonitrile, such as 0-0.4 eq.

In a further embodiment the solvent system together with the dissolved 4-[4-(dimethylamino)-1-(4'-fluorophenyl)-1-hydroxybutyl]-3-(hydroxymethyl)-benzonitrile and (+)-(S,S)— or (−)-(R,R)—O,O'-di-p-toluoyl-tartaric acid is cooled from a first temperature in the range from 20° C. to the reflux temperature for the solvent system, particularly 25° C. to 70° C., more particularly 30° C. to 50° C., to a second temperature in the range of 0° C. to 40° C., particularly 10° C. to 30° C., more particularly 15° C. to 25° C. In a particular embodiment the difference between the first and the second temperature is in the range of 5° C. to 50° C., particularly 10° C. to 40° C., more particularly 15° C. to 30° C.

In a particular embodiment the mixture of 4-[4-(dimethylamino)-1-(4'-fluorophenyl)-1-hydroxybutyl]-3-(hydroxymethyl)-benzonitrile, (+)-(S,S)— or (–)—(R,R)—O,O'-di-p-toluoyl-tartaric acid and solvent system is kept at the first temperature for a period in the range of 0-4 hours before cooling, more particularly 0.5-3 hours, and most particularly 1-2 hours.

In another particular embodiment the mixture of 4-[4-(dimethylamino)-1-(4'-fluoro-phenyl)-1-hydroxybutyl]-3-(hydroxymethyl)-benzonitrile, (+)-(S,S)— or (–)-(R,R)—O,O'-di-p-toluoyl-tartaric acid and solvent system is seeded with crystals of the desired salt at the first temperature or during cooling. Typically the amount of seeding crystals is in the range of 0.4-0.8 g seeding crystals/kg 4-[4-(dimethylamino)-1-(4'-fluorophenyl)-1-hydroxybutyl]-3-(hydroxymethyl)-benzonitrile, more typically in the range of 0.45-0.7 g/kg, most typically in the range of 0.5-0.6 g/kg.

In an equally particular embodiment the cooling is done within 8 hours, particularly within 4 hours, more particularly within 2 hours. In another equally particular embodiment the precipitated salt is separated from the mother liquor within 8 hours after onset of precipitation, more particularly within 4 hours. In yet an equally particular embodiment the separated salt is washed within 4 hours, more particularly within 2 hours.

In yet a further embodiment the separated salt is re-slurried or recrystallized one or more times in a solvent system comprising 1-propanol or ethanol by heating to a temperature in the range from 30° C. to the reflux temperature for the solvent, more particularly 40° C. to 60° C., followed by cooling to a temperature in the range of 0° C. to 40° C., particularly 10° C. to 30° C., more particularly 15° C. to 25° C. In a particular embodiment 1-propanol or ethanol is the major constituent of the solvent system. In a more particular embodiment 1-propanol or ethanol constitutes at least 50% of the solvent system, such as at least 75%, at least 90% or at least 95%, and in a most particular embodiment 1-propanol or ethanol is the only solvent. In a particular embodiment the major constituent of the solvent system used for re-slurrying is the same as the major constituent of the solvent system used for crystallization.

Another aspect of the present invention is to provide a method for manufacture of escitalopram comprising resolution of 4-[4-(dimethylamino)-1-(4'-fluorophenyl)-1-hydroxybutyl]-3-(hydroxymethyl)-benzonitrile into its enantiomers as described above.

In one embodiment one of the isolated enantiomers of 4-[4-(dimethylamino)-1-(4'-fluorophenyl)-1-hydroxybutyl]-3-(hydroxymethyl)-benzonitrile is stereoselectively transformed into escitalopram.

In a particular embodiment S-4-[4-(dimethylamino)-1-(4'-fluorophenyl)-1-hydroxybutyl]-3-(hydroxymethyl)-benzonitrile is stereoselectively transformed into escitalopram.

In a more particular embodiment the S-4-[4-(dimethylamino)-1-(4'-fluorophenyl)-1-hydroxybutyl]-3-(hydroxymethyl)-benzonitrile is reacted with a reactive acid derivative such as an acid chloride or acid anhydride, in particular methane sulfonylchloride or p-toluene sulfonylchloride, in the presence of a base, such as triethylamine or pyridine.

As used throughout the description and claims the terms "resolution" and "resolved" refer to a process wherein the enantiomeric purity of a racemic or non-racemic mixture of enantiomers is increased, such as a process wherein the proportion of the unwanted enantiomer in the mixture is reduced by at least 20% provided that the enantiomer ratio in the resulting mixture is in favour of the wanted enantiomer as exemplified by the following two examples:

i) a racemic mixture (50:50) is transformed into a mixture with an enantiomer ratio of at least 60:40, or ii) a 80:20 mixture is transformed into a mixture with an enantiomer ratio of at least 84:16.

As used throughout the description and claims the term "a racemic mixture" means a 50:50 mixture of enantiomers, whereas the term "a non-racemic mixture" means any mixture of enantiomers that is not 50:50.

As used throughout the description and claims the term "isolated enantiomer" means an enantiomer that is at least 95% enantiomerically pure, particularly at least 97% enantiomerically pure, more particularly at least 98% enantiomerically pure, and most particularly at least 99% enantiomerically pure.

As used throughout the description and claims the term "fractional crystallisation" means a process wherein one enantiomer crystallizes as a salt with a chiral acid preferentially over the other enantiomer and in said process the crystallization may start from a solution of the salt or a suspension of the salt.

As used throughout the description and claims the term "solvent system" means the combination of organic solvents and water, when present. The term "organic solvent" encompasses any protic or aprotic solvent, such as alcohols, esters, alkanes, ethers and aromatics but excludes acids such as carboxylic acids and bases such as amines.

As used throughout the description and claims the term "re-slurried" refers to a process wherein the crystalline material is suspended in a solvent at a temperature whereby the crystalline material dissolves partially followed by cooling whereupon the dissolved material crystallizes partially again.

As used throughout the description and claims the term "recrystallized" refers to a process wherein the crystalline material is dissolved in a solvent at a temperature, optionally filtered to remove insoluble material, and followed by cooling whereupon the dissolved material crystallizes partially again.

If the chiral purity of an S- or R-4-[4-(dimethylamino)-1-(4'-fluorophenyl)-1-hydroxybutyl]-3-(hydroxymethyl)-benzonitrile product resulting from the method as disclosed herein is not sufficiently high which may occur inter alia when using mother liquor as the product, the chiral purity may be further improved by precipitation of racemic 4-[4-(dimethylamino)-1-(4'-fluorophenyl)-1-hydroxybutyl]-3-(hydroxymethyl)-benzonitrile from a solution of the product enriched in S- or R-4-[4-(dimethylamino)-1-(4'-fluorophenyl)-1-hydroxybutyl]-3-(hydroxymethyl)-benzonitrile leaving a further enriched S- or R-4-[4-(dimethylamino)-1-(4'-fluorophenyl)-1-hydroxybutyl]-3-(hydroxymethyl)-benzonitrile in solution as disclosed in WO2004/056754.

S-4-[4-(dimethylamino)-1-(4'-fluorophenyl)-1-hydroxybutyl]-3-(hydroxymethyl)-benzonitrile may be stereoselectively transformed into escitalopram as disclosed in EP0347066.

R-4-[4-(dimethylamino)-1-(4'-fluorophenyl)-1-hydroxybutyl]-3-(hydroxymethyl)-benzonitrile may be transformed into escitalopram as disclosed in WO03/000672.

If the chiral purity of an S-citalopram product resulting from the method as disclosed herein is not sufficiently high which may occur inter alia when using mother liquor as the product, the chiral purity may be further improved by precipitation of racemic citalopram from a solution of the product enriched in S-citalopram leaving a further enriched S-citalopram in solution as disclosed in WO2003/000672.

Experimental Section

Throughout the description and claims the following abbreviations are used:

Eq means equivalents and is calculated as the molar ratio relative to the amount of 4-[4-(dimethylamino)-1-(4'-fluorophenyl)-1-hydroxybutyl]-3-(hydroxymethyl)-benzonitrile.

V means volumes and is calculated as milliliter solvent per gram of 4-[4-(dimethyl-amino)-1-(4'-fluorophenyl)-1-hydroxybutyl]-3-(hydroxymethyl)-benzonitrile free base.

Molar yield is calculated as mol S-4-[4-(dimethylamino)-1-(4'-fluorophenyl)-1-hydroxybutyl]-3-(hydroxymethyl)-benzonitrile in the product per mol racemic 4-[4-(dimethylamino)-1-(4'-fluorophenyl)-1-hydroxybutyl]-3-(hydroxymethyl)-benzonitrile starting material.

Seeding Crystals

Seeding crystals can be prepared by mixing of a solution of S-4-[4-(dimethylamino)-1-(4'-fluorophenyl)-1-hydroxybutyl]-3-(hydroxymethyl)-benzonitrile (10 g) in 1-propanol (9.5 mL) with a solution of (+)-O,O'-di-p-toluoyl-(S,S)-tartaric acid (11.6 g) in 1-propanol (88 ml) or by mixing of a solution of R-4-[4-(dimethylamino)-1-(4'-fluorophenyl)-1-hydroxybutyl]-3-(hydroxymethyl)-benzonitrile (10 g) in 1-propanol (9.5 mL) with a solution of (−)-O,O'-di-p-toluoyl-(R,R)-tartaric acid (11.6 g) in 1-propanol (88 ml). Alternatively seeding crystals may be made in a similar way using ethanol as the solvent instead of 1-propanol. Preferably the seeding crystals are crystallized from the same solvent as the one for the crystallization where they shall be used. Crystals produced according to the examples below may also be used as seeding crystals.

The S- or R-4-[4-(dimethylamino)-1-(4'-fluorophenyl)-1-hydroxybutyl]-3-(hydroxyl-methyl)-benzonitrile used for the preparation of seeding crystals can be obtained as disclosed in EP0347066 or WO03/006449.

Experiment 1

(+)-O,O'-Di-p-toluoyl-(S,S)-tartaric acid (0.39 eq) was dissolved in 1-propanol (3.44 V). The mixture was heated up to ca. 40° C. and acetic acid (0.2 eq.) was added. This solution was transferred within one hour to a solution of 4-[4-(dimethylamino)-1-(4'-fluorophenyl)-1-hydroxybutyl]-3-(hydroxymethyl)-benzonitrile free base in 1-propanol (0.95 V) containing 0.1 V of toluene. The resolution mixture, containing now in total 4.4 V 1-propanol was seeded with seed crystals comprising S-4-[4-(dimethylamino)-1-(4'-fluorophenyl)-1-hydroxybutyl]-3-(hydroxymethyl)-benzonitrile and (+)-O,O'-di-p-toluoyl-(S,S)-tartaric acid and then stirred at 40° C. for 2 hours. The mixture was cooled to 20-25° C. within 2 hours. The product was filtered and washed twice with 1-propanol. The enantiomeric purity was typically in the range from about 91% to about 98% S.

The product was re-slurried in 1-propanol (2.5 V) at around 50° C. for 2 hours. The mixture was cooled to 20-25° C. The product was filtered and washed with 1-propanol. The enantiomeric purity was typically about 99.3% S.

The molar yield was typically 34-36%.

Experiment 2

(+)-O,O'-Di-p-toluoyl-(S,S)-tartaric acid (0.4 eq) was dissolved in 1-propanol (3.5 V). The mixture was heated up to ca. 40° C., acetic acid (0.2 eq.) was added and then the solution is transferred to a solution of 4-[4-(dimethylamino)-1-(4'-fluorophenyl)-1-hydroxybutyl]-3-(hydroxymethyl)-benzonitrile free base in 1-propanol containing 0.1 V toluene. The resolution mixture, containing now in total 4.5 V 1-propanol was seeded with seed crystals comprising S-4-[4-(dimethylamino)-1-(4'-fluorophenyl)-1-hydroxybutyl]-3-(hydroxymethyl)-benzonitrile and (+)—O,O'-di-p-toluoyl-(S,S)-tartaric acid and then stirred at 40° C. for two hours. The mixture was cooled to 20-25° C. in two hours. The product was filtered (filter reactor) and washed with 1-propanol.

The enantiomeric purity was typically around 97% S or higher.

An exemplary batch gave molar yield: 33.8%, enantiomeric purity: 99.0% S.

Experiment 3

The general procedure of Experiment 2 was applied, however 0.5 eq of (+)-O,O'-di-p-toluoyl-(S,S)-tartaric acid and 10V of 1-propanol were used. No toluene or acetic acid was present in the system.

An exemplary batch gave molar yield: 29.5%; enantiomeric purity: 99.2% S.

Experiment 4

The general procedure of Experiment 2 was applied. To the 4-[4-(dimethylamino)-1-(4'-fluorophenyl)-1-hydroxybutyl]-3-(hydroxymethyl)-benzonitrile free base solution in 1-propanol was added 0.05 V of water. No toluene or acetic acid was present in the system.

An exemplary batch gave molar yield: 29.3%; enantiomeric purity: 99.3% S.

Experiment 5

The general procedure of Experiment 2 was applied using only 0.25 eq of (+)-O,O'-di-p-toluoyl-(S,S)-tartaric acid. No acetic acid was present in the system.

An exemplary batch gave molar yield: 29.4%; enantiomeric purity: 99.0% S.

Experiment 6

The general procedure of Experiment 2 was applied. No acetic acid was present in the system.

An exemplary batch gave molar yield: 32.6%; enantiomeric purity: 98.0% S.

Experiment 7

The general procedure of Experiment 2 was applied. No acetic acid was present in the system. The experiment was carried out with a small amount of water (0.01V)

An exemplary batch gave molar yield: 32.5%; enantiomeric purity: 98.7% S.

Experiment 8

The general procedure of Experiment 2 was applied. No acetic acid was present in the system. The experiment was carried out with a higher amount of water (0.05V)

Exemplary batches gave: Molar yield: 34.7%; enantiomeric purity: 99.0% S.

Experiment 9

The general procedure of Experiment 2 was applied. Additionally a small amount of water (0.05 V) was added to the 4-[4-(dimethylamino)-1-(4'-fluorophenyl)-1-hydroxybutyl]-3-(hydroxymethyl)-benzonitrile free base solution in 1-propanol.

An exemplary batch gave molar yield: 33.0%; enantiomeric purity: 99.1% S.

Experiment 10

100 g (0.292 moles) of 4-(4-dimethylamino-1-(4'-fluorophenyl)-1-hydroxybutyl)-3-(hydroxymethyl)-benzonitrile were dissolved in 150 ml of pure ethanol at 40° C. Maintaining the temperature around 40° C., a solution made of 57.5 g (0.148 moles) of (+)-O,O'-di-p-toluoyl-(S,S)-tartaric acid and 350 ml of pure ethanol was added in one hour. The mixture was seeded and then cooled to room temperature overnight. The suspension was cooled to 0° C. and then filtered.

Molar yield 29.5%, enantiomeric purity 98.2% S.

Experiment 11

(+)-O,O'-Di-p-toluoyl-(S,S)-tartaric acid (0.25 eq) was dissolved in 1-propanol (200 ml). The mixture was heated up to ca. 40° C. and then the solution was transferred to a solution of 4-[4-(dimethylamino)-1-(4'-fluorophenyl)-1-hydroxybutyl]-3-(hydroxyl-methyl)-benzonitrile free base (100 g) in 1-propanol (100 ml) containing 11 g toluene. The resolution mixture, containing now in total 3 V 1-propanol was seeded at 40° C. with seed crystals comprising S-4-[4-(dimethylamino)-1-(4'-fluorophenyl)-1-hydroxybutyl]-3-(hydroxymethyl)-benzonitrile and (+)-O,O'-di-p-toluoyl-(S,S)-tartaric acid and then stirred at 40° C. for two hours. The mixture was cooled to 20° C. in two hours and kept at 20° C. overnight. The product was filtered (filter reactor) and washed with 1-propanol.

Molar yield: 31.8%, enantiomeric purity: 95.5% S.

Experiment 12

Experiment 11 was repeated except that the total volume of 1-propanol was 10 V.

Molar yield: 30.7%, enantiomeric purity: 98.9% S.

Experiment 13

Experiment 11 was repeated except that the total volume of 1-propanol was 4.3 V and 0.39 eq of (+)-O,O'-di-p-toluoyl-(S,S)-tartaric acid was used. This example was repeated several times. The crystallization batches were kept at 20° C. for up to 16 h, typically up to 8 h.

Molar yields: about 35%, enantiomeric purity: >98% S.

Experiment 14

Experiment 11 was repeated except that the total volume of 1-propanol was 4.5 V, 0.50 eq of (+)-O,O'-di-p-toluoyl-(S,S)-tartaric acid was used, and the holding time before filtration was 0.5 h.

Molar yield: 36%, enantiomeric purity: 97.2% S.

Experiment 15

Experiment 11 was repeated except that the total volume of 1-propanol was 4.4 V, 0.60 eq of (+)-O,O'-di-p-toluoyl-(S,S)-tartaric acid was used, and the holding time before filtration was 0.5 h.

Molar yield: 38.9%, enantiomeric purity: 82.8% S.

Experiment 16

Experiment 11 was repeated except that the total volume of 1-propanol was 4.5 V, 0.675 eq of (+)-O,O'-di-p-toluoyl-(S,S)-tartaric acid was used, and the holding time before filtration was overnight.

Molar yield: 35.2%, enantiomeric purity: 76.2% S.

Experiment 17

Experiment 11 was repeated except that the total volume of 1-propanol was 6 V, 0.75 eq of (+)-O,O'-di-p-toluoyl-(S,S)-tartaric acid was used, and the holding time before filtration was 0.5 h.

Molar yield: 24.8%, enantiomeric purity: 99.4% S.

Experiment 18

Experiment 11 was repeated except that the total volume of 1-propanol was 6 V, 0.75 eq of (+)-O,O'-di-p-toluoyl-(S,S)-tartaric acid was used, and the holding time before filtration was overnight.

Molar yield: 31%, enantiomeric purity: 99.4% S.

Experiment 19

Experiment 11 was repeated except that the total volume of 1-propanol was 4.5 V, 0.75 eq of (+)-O,O'-di-p-toluoyl-(S,S)-tartaric acid was used, and the holding time before filtration was overnight.

Molar yield: 30.3%, enantiomeric purity: 99.0% S.

Experiment 20

Experiment 11 was repeated except that the total volume of 1-propanol was 4.5 V, 0.75 eq of (+)-O,O'-di-p-toluoyl-(S,S)-tartaric acid was used, and the holding time before filtration was 4 days.

Molar yield: 32.2%, enantiomeric purity: 92.8% S.

Experiment 21

Experiment 11 was repeated except that acetonitrile was used as the solvent in stead of 1-propanol in a total volume of 10 V, 0.25 eq of (+)-O,O'-di-p-toluoyl-(S,S)-tartaric acid was used, and the holding time before filtration was overnight.

Molar yield: 30.0%, enantiomeric purity: 96.0% S.

Experiment 22

Experiment 11 was repeated except that acetonitrile was used as the solvent in stead of 1-propanol in a total volume of 4.5 V, 0.50 eq of (+)-O,O'-di-p-toluoyl-(S,S)-tartaric acid was used, and the holding time before filtration was overnight.

Molar yield: 24.7%, enantiomeric purity: 99.2% S.

Experiment 23

Experiment 11 was repeated except that a mixture of 1-propanol and dichloromethane (50:50) was used as the solvent in stead of 1-propanol in a total volume of 2 V (The (+)-O,O'-di-p-toluoyl-(S,S)-tartaric acid and 4-[4-(dimethylamino)-1-(4'-fluoro-phenyl)-1-hydroxybutyl]-3-(hydroxylmethyl)-benzonitrile free base were dissolved in 4.5 V dichloromethane, 3.5 V dichloromethane was distilled off and 1 V 1-propanol was added), 0.25 eq of (+)-O,O'-di-p-toluoyl-(S,S)-tartaric acid was used, and the holding time before filtration was overnight.
Molar yield: 18.5%, enantiomeric purity: 96.9% S.

Experiment 24

Experiment 11 was repeated except that a mixture of 1-propanol and dichloromethane (95:5) was used as the solvent in stead of 1-propanol in a total volume of 4.5 V, 0.35 eq of (+)-O,O'-di-p-toluoyl-(S,S)-tartaric acid was used, and the holding time before filtration was overnight.
Molar yield: 35.7%, enantiomeric purity: 78.8% S.

Experiment 25

Experiment 11 was repeated except that a mixture of 1-propanol and dichloromethane (85:15) was used as the solvent in stead of 1-propanol in a total volume of 4.5 V, 0.4 eq of (+)-O,O'-di-p-toluoyl-(S,S)-tartaric acid was used, and the holding time before filtration was overnight.
Molar yield: 31%, enantiomeric purity: 98.2% S.

Experiment 26

Experiment 11 was repeated except that a mixture of 1-propanol and dichloromethane (50:50) was used as the solvent in stead of 1-propanol in a total volume of 4.4 V, 0.5 eq of (+)-O,O'-di-p-toluoyl-(S,S)-tartaric acid was used, and the holding time before filtration was overnight.
Molar yield: 16.4%, enantiomeric purity: 98.9% S.

Experiment 27

Experiment 11 was repeated except that a mixture of 1-propanol and dichloromethane (75:25) was used as the solvent in stead of 1-propanol in a total volume of 4.5 V, 0.5 eq of (+)-O,O'-di-p-toluoyl-(S,S)-tartaric acid was used, and the holding time before filtration was overnight.
Molar yield: 34.2%, enantiomeric purity: 98.8% S.

Experiment 28

Experiment 11 was repeated except that the crystallization mixture did not contain toluene, a mixture of 1-propanol and dichloromethane (85:15) was used as the solvent in stead of 1-propanol in a total volume of 4.5 V, 0.5 eq of (+)-O,O'-di-p-toluoyl-(S,S)-tartaric acid was used, and the holding time before filtration was overnight.
Molar yield: 37.8%, enantiomeric purity: 98.8% S.

Experiment 29

Experiment 11 was repeated except that a mixture of 1-propanol and dichloromethane (85:15) was used as the solvent in stead of 1-propanol in a total volume of 4.5 V, 0.5 eq of (+)-O,O'-di-p-toluoyl-(S,S)-tartaric acid was used, and the holding time before filtration was overnight.
Molar yield: 36.6%, enantiomeric purity: 97.6% S.

Experiment 29

Experiment 11 was repeated except that a mixture of 1-propanol and dichloromethane (90:10) was used as the solvent in stead of 1-propanol in a total volume of 4.5 V, 0.5 eq of (+)-O,O'-di-p-toluoyl-(S,S)-tartaric acid was used, and the holding time before filtration was overnight. This experiment was performed twice with the following results.
Molar yield: 38.9%, enantiomeric purity: 97.7% S.
Molar yield: 35.8%, enantiomeric purity: 98.5% S.

Experiment 30

Experiment 11 was repeated except that a mixture of 1-propanol and dichloromethane (92.5:7.5) was used as the solvent in stead of 1-propanol in a total volume of 6.0 V, 0.5 eq of (+)-O,O'-di-p-toluoyl-(S,S)-tartaric acid was used, and the holding time before filtration was overnight. This experiment was performed twice with the following results.
Molar yield: 35.1%, enantiomeric purity: 98.6% S.
Molar yield: 39.0%, enantiomeric purity: 81.3% S.

Experiment 31

Experiment 11 was repeated except that a mixture of 1-propanol and dichloromethane (95:5) was used as the solvent in stead of 1-propanol in a total volume of 4.5 V, 0.5 eq of (+)-O,O'-di-p-toluoyl-(S,S)-tartaric acid was used, and the holding time before filtration was 0.5 h.
Molar yield: 35.0%, enantiomeric purity: 98.4% S.

Experiment 32

Experiment 11 was repeated except that a mixture of 1-propanol and dichloromethane (90:10) was used as the solvent in stead of 1-propanol in a total volume of 4.6 V, 0.6 eq of (+)-O,O'-di-p-toluoyl-(S,S)-tartaric acid was used, and the holding time before filtration was overnight.
Molar yield: 38.5%, enantiomeric purity: 99.1% S.

Experiment 33

Experiment 11 was repeated except that a mixture of 1-propanol and acetonitrile (15:85) was used as the solvent in stead of 1-propanol in a total volume of 4.5 V, 0.5 eq of (+)-O,O'-di-p-toluoyl-(S,S)-tartaric acid was used, and the holding time before filtration was 0.5 h.
Molar yield: 25.9%, enantiomeric purity: 99.2% S.

Experiment 34

Experiment 11 was repeated except that a mixture of 1-propanol and acetonitrile (85:15) was used as the solvent in stead of 1-propanol in a total volume of 4.5 V, 0.5 eq of (+)-O,O'-di-p-toluoyl-(S,S)-tartaric acid was used, and the holding time before filtration was overnight.
Molar yield: 18.5%, enantiomeric purity: 99.4% S.

Experiment 35

Experiment 11 was repeated except that a mixture of 1-propanol and acetonitrile (90:10) was used as the solvent in stead of 1-propanol in a total volume of 4.5 V, 0.5 eq of (+)-O,O'-di-p-toluoyl-(S,S)-tartaric acid was used, and the holding time before filtration was overnight.
Molar yield: 29.9%, enantiomeric purity: 99.3% S.

Experiment 36

Experiment 11 was repeated except that a mixture of 1-propanol and ethylacetate (31:69) was used as the solvent in stead of 1-propanol in a total volume of 4.5 V whereupon extra 2 V 1-propanol was added, 0.25 eq of (+)-O,O'-di-p-toluoyl-(S,S)-tartaric acid was used, and the holding time before filtration was 0.5 h.

Molar yield: 28.6%, enantiomeric purity: 98.4% S.

Experiment 37

Experiment 11 was repeated except that a mixture of 1-propanol and ethanol (50:50) was used as the solvent in stead of 1-propanol in a total volume of 4.4 V, 0.5 eq of (+)-O,O'-di-p-toluoyl-(S,S)-tartaric acid was used, and the holding time before filtration was 0.5 h.

Molar yield: 27.4%, enantiomeric purity: 99.4% S.

Experiment 38

A range of experiments were conducted examining the resolution of diol with (+)—(S,S)-DTT. The general procedure is described below, and the details and results for each reaction are in table 1.

Racemic diol (20 g, 58.4 mmol) was dissolved in approximately half of the solvent used for the experiment at 40° C. (+)-(S,S)-DTT.H$_2$O (quantity specified in the table) was added as a solution in the other half of the solvent. The solution was held at 40° C. and was seeded within two minutes with crystals of (S)-diol.½(+)-(S,S)-DTT (approximately 5 mg). Crystallization typically began within 5-10 minutes after seeding. After 2 h at 40° C., the temperature of the solution was lowered to 20° C. over 2 h, and the solution was held at this temperature for a further 1 h. The product was then separated by filtration, washed with the appropriate solvent (2×20 mL) and dried overnight at 60° C. under reduced pressure.

TABLE 1

Results of experiment 38

| Experiment Number | Solvent or solvent mixtures (mixtures are expressed as v/v %) | Total volume solvent used (mL) | Equivalents DTT used | Yield (%) | Ratio S/R |
|---|---|---|---|---|---|
| 38a | 1-propanol | 60 | 0.25 | 16.7 | 96.0/4.0 |
| 38b | 1-propanol | 86 | 0.39 | 19.9 | 97.0/3.0 |
| 38c | 1-propanol | 90 | 0.5 | 26 | 77.3/22.7 |
| 38d | 1-propanol | 90 | 0.68 | 15.8 | 98.4/1.6 |
| 38e | 1-propanol | 120 | 0.75 | 11.5 | 96.6/3.4 |
| 38f | Acetonitrile | 200 | 0.25 | 9.4 | 91.8/8.2 |
| 38g | Acetonitrile | 90 | 0.5 | 17.2 | 78.7/21.3 |
| 38h | 1-propanol/acetonitrile (15/85) | 90 | 0.5 | 14.2 | 99.3/0.7 |
| 38i | 1-propanol/acetonitrile (85/15) | 90 | 0.5 | 9.8 | 99.0/1.0 |
| 38j | 1-propanol/acetonitrile (90/10) | 90 | 0.5 | 13.9 | 99.4/0.6 |
| 38k | 1-propanol/ethyl acetate (31/69) | 90 | 0.25 | 15.1 | 94.0/6.0 |
| 38l | 1-propanol/ethanol (50/50) | 90 | 0.5 | 15.4 | 99.3/0.7 |
| 38m | 1-propanol/DCM (50/50) | 40 | 0.25 | 11.7 | 96.0/4.0 |
| 38n | 1-propanol/DCM (85/15) | 90 | 0.4 | 34.6 | 98.6/1.4 |
| 38o | 1-propanol/DCM (75/25) | 90 | 0.5 | 26.6 | 98.4/1.6 |
| 38p | 1-propanol/DCM (85/15) | 90 | 0.5 | 33.7 | 98.8/1.2 |
| 38q | 1-propanol/DCM (90/10) | 90 | 0.5 | 35.8 | 99.3/0.7 |
| 38r | 1-propanol/DCM (92.5/7.5) | 120 | 0.5 | 37.6 | 99.0/1.0 |
| 38s | 1-propanol/DCM (95/5) | 90 | 0.5 | 36.6 | 99.4/0.6 |
| 38t | 1-propanol/DCM (90/10) | 90 | 0.6 | 29.6 | 99.1/0.9 |
| 38u | Ethanol/DCM (50/50) | 60 | 0.5 | 0 | n/a |
| 38v | Ethanol/DCM (75/25) | 90 | 0.5 | 0.7 | 96.5/3.5 |
| 38w | Ethanol/DCM (85/15) | 90 | 0.5 | 9.9 | 98.8/1.2 |
| 38x | Ethanol | 100 | 0.5 | 20.7 | 99.6/0.4 |

Although the experiments above all have been performed using (+)-O,O'-di-p-toluoyl-(S,S)-tartaric acid which precipitates together with S-4-[4-(dimethylamino)-1-(4'-fluorophenyl)-1-hydroxybutyl]-3-(hydroxymethyl)-benzonitrile leaving the mother liquor enriched in R-4-[4-(dimethylamino)-1-(4'-fluorophenyl)-1-hydroxybutyl]-3-(hydroxymethyl)-benzonitrile, the skilled person will see that he could as well use (−)-O,O'-di-p-toluoyl-(R,R)-tartaric acid which precipitates together with R-4-[4-(dimethylamino)-1-(4'-fluorophenyl)-1-hydroxybutyl]-3-(hydroxymethyl)-benzonitrile leaving the mother liquor enriched in S-4-[4-(dimethylamino)-1-(4'-fluorophenyl)-1-hydroxybutyl]-3-(hydroxymethyl)-benzonitrile.

Although the standard mode of addition is: (+)-O,O'-di-p-toluoyl-(S,S)-tartaric acid added to 4-[4-(dimethylamino)-1-(4'-fluorophenyl)-1-hydroxybutyl]-3-(hydroxyl-methyl)-benzonitrile; this addition procedure can be inverted (4-[4-(dimethylamino)-1-(4'-fluorophenyl)-1-hydroxybutyl]-3-(hydroxymethyl)-benzonitrile added to (+)-O,O'-di-p-toluoyl-(S,S)-tartaric acid).

The invention claimed is:

1. A method for resolution of 4-[4-(dimethylamino)-1-(4'-fluorophenyl)-1-hydroxybutyl]-3-(hydroxymethyl)-benzonitrile as a racemic or non-racemic enantiomer mixture into its isolated enantiomers, said method comprising the step of fractionally crystallising 4-[4-(dimethylamino)-1-(4'fluorophenyl)1-hydroxybutyl]-3-(hydroxymethyl)-benzonitrile as a salt with the (+)-(S,S) or (−)-(R,R)-enantiomer of O,O'-di-p-toluoyl-tartaric acid in a solvent system wherein 1-propanol constitutes at least 50% of the solvent system.

2. A method according to claim 1 wherein not more than 1 mol of the (+)-(S,S) or (−)-(R,R)-enantiomer of O,O'-di-p-toluoyl-tartaric acid is used per mol 4-[4-(dimethylamino)-1-(4'-fluorophenyl)-1-hydroxybutyl]-3-(hydroxymethyl)-benzonitrile.

3. A method according to claim 1 wherein (+)-O,O'-di-p-toluoyl-(S,S)-tartaric acid is used.

4. A method according to claim 1 wherein (−)-O,O'-di-p-toluoyl-(R,R)-tartaric acid is used.

5. A method according to claim 1 wherein the solvent system comprises one or more organic co-solvents.

6. A method according to claim 1 wherein the solvent system comprises water.

7. A method according to claim 1 wherein the solvent system comprises an achiral acid which is capable of protonating 4-[4-(dimethylamino)-1-(4'-fluorophenyl)-1-hydroxybutyl]-3-(hydroxymethyl)-benzonitrile but does not precipitate the 4-[4-(dimethylamino)-1-(4'-fluorophenyl)-1-hydroxybutyl]-3-(hydroxymethyl)-benzonitrile as a salt in the present conditions.

8. A method according to claim 7 wherein the achiral acid is an organic acid.

9. A method according to claim 1 wherein the solvent system together with the dissolved 4-[4-(dimethylamino)-1-(4'-fluorophenyl)-1-hydroxybutyl]-3-(hydroxymethyl)-benzonitrile and (+)-(S,S)— or (−)-(R,R)—O,O'-di-p-toluoyl-tartaric acid is cooled from a first temperature in the range from 20° C. to the reflux temperature for the solvent system to a second temperature in the range of 0° C. to 40° C.

10. A method according to claim 9 wherein the mixture of 4-[4-(dimethylamino)-1-(4'-fluorophenyl)-1-hydroxybutyl]-3-(hydroxymethyl)-benzonitrile, (+)-(S,S)— or (−)-(R,R)—O,O'-di-p-toluoyl-tartaric acid and solvent system is kept at the first temperature for a period in the range of 0-4 hours before cooling.

11. A method according to claim 9 wherein the mixture of 4-[4-(dimethylamino)-1-(4'-fluorophenyl)-1-hydroxybutyl]-3-(hydroxymethyl)-benzonitrile, (+)-(S,S)— or (−)-(R,R)—O,O'-di-p-toluoyl-tartaric acid and solvent system is seeded with crystals of the desired salt at the first temperature or during cooling.

12. A method according to claim 9 wherein the cooling is done within 8 hours.

13. A method according to claim 1 wherein the precipitated salt is separated from the mother liquor within 8 hours after onset of precipitation.

14. A method according to claim 1 wherein the separated salt is washed within 4 hours.

15. A method according to claim 1 wherein the separated salt is re-slurried or recrystallised one or more times in a solvent system comprising 1-propanol or ethanol by heating to a temperature in the range from 30° C. to the reflux temperature for the solvent followed by cooling to a temperature in the range of 0° C. to 40° C.

16. A method for manufacture of escitalopram comprising the method of claim 1.

17. A method according to claim 16 further comprising a stereoselective transformation of one of the isolated enantiomers of 4-[4-(dimethylamino)-1-(4'-fluorophenyl)-1-hydroxybutyl]-3-(hydroxymethyl)-benzonitrile into escitalopram.

18. A method according to claim 17 wherein S-4-[4-(dimethylamino)-1-(4'-fluorophenyl)-1-hydroxybutyl]-3-(hydroxymethyl)-benzonitrile is stereoselectively transformed into escitalopram.

19. A method according to claim 18 wherein the S-4-[4-(dimethylamino)-1-(4'-fluorophenyl)-1-hydroxybutyl]-3-(hydroxymethyl)-benzonitrile is reacted with an acid chloride or an acid anhydride in the presence of a base.

20. A method according to claim 5 wherein the organic co-solvent is toluene, diethylether, ethyl acetate or dichloromethane.

21. A method according to claim 8 wherein the organic acid is formic acid, acetic acid, trifluoroacetic acid or methanesulfonic acid.

22. A method according to claim 19, wherein the acid chloride is methyl sulfonylchloride or p-toluene sulfonylchloride and the base is triethylamine or pyridine.

* * * * *